United States Patent [19]

Rideout et al.

[11] Patent Number: 4,481,197

[45] Date of Patent: Nov. 6, 1984

[54] ANTI-INFLAMMATORY DEOXYRIBOSIDES

[75] Inventors: Janet L. Rideout, Raleigh; Thomas A. Krenitsky, Chapel Hill, both of N.C.

[73] Assignee: Burroughs Wellcome Co., Research Triangle Park, N.C.

[21] Appl. No.: 389,561

[22] Filed: Jun. 17, 1982

Related U.S. Application Data

[62] Division of Ser. No. 143,836, Apr. 25, 1980, Pat. No. 4,381,344.

[51] Int. Cl.$^3$ ..................... A61K 31/70; C07H 17/00; C07H 15/12
[52] U.S. Cl. ..................................... 424/180; 536/24; 536/26; 536/27; 536/28
[58] Field of Search ....................... 536/26, 27, 28, 24; 424/180

[56] References Cited

U.S. PATENT DOCUMENTS

| | | | |
|---|---|---|---|
| 4,056,674 | 11/1977 | Robins et al. | 536/28 |
| 4,210,639 | 7/1980 | Chiang et al. | 536/26 |
| 4,309,419 | 1/1982 | Wolberg et al. | 536/24 |
| 4,322,411 | 3/1982 | Vinegar et al. | 424/180 |

OTHER PUBLICATIONS

Chem. Abstracts 95:81396v, (1981).
Chem. Abstracts 96:91647n, (1982).
Chem. Abstracts 96:120885w, (1982).

Primary Examiner—Ethel G. Love
Attorney, Agent, or Firm—Donald Brown

[57] ABSTRACT

The novel compounds 3-deaza-2'-deoxyadenosine and certain of its derivatives and their pharmaceutically acceptable salts have anti-inflammatory activity as well as immune response suppression activity. 3-Deaza-2'-deoxyadenosine and certain of its intermediates are synthesized by the enzyme catalyzed reaction of the appropriately substituted 3-deazapurine with a 2'-deoxyribose donor.

11 Claims, No Drawings

ANTI-INFLAMMATORY DEOXYRIBOSIDES

This is a division of application Ser. No. 143,836 filed Apr. 25, 1980, U.S. Pat. No. 4,381,344.

The present invention relates to the novel, anti-inflammatory compound, 4-amino-1-(2-deoxy-β-d-ribofuranosyl)-1H-imidazo-[4,5-c]-pyridine and to certain derivatives, to pharmaceutical formulations of the compound or its derivatives, and to their use in medicine.

U.S. Pat. No. 4,148,888 discloses 3-deazaadenosine as an antiviral and antifocal agent.

European Patent Application No. 79 103 947.2 discloses 3-deazaadenosine as an immunosuppressant.

French Patent No. 1 324 011 discloses an improved chemical synthesis of nuclcosides. These are stated to have antibiotic activity and to be "pharmacologically important" but no activity is substantiated in the specification. Particular compounds within the generality are stated to have antibacterial, cytostatic, virus mutagenic and deoxyribonuclcoside synthesis inhibiting properties. Furthermore, there is no indication in that patent that any of the compounds disclosed have anti-inflammatory or immunosuppressive activity.

It has now been surprisingly found that 3-deaza-2'-deoxyadenosine, i.e. 4-amino-1-(2-deoxy-β-D-ribofuranosyl)-1H-imidazo-[4,5-c]-pyridine and certain derivatives thereof possess anti-inflammatory activity and are thus useful in the treatment of inflammation. In addition these compounds have been found to have immunosuppressive activity and are therefore useful whenever it is desirable to suppress the immune response of a patient.

Accordingly, the present invention provides, in a first aspect, the compound of formula (I),

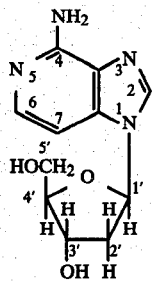

the 5'-phosphate ester thereof, organic esters of the compound or its 5'-phosphate ester, and pharmaceutically acceptable salts of the compound or its esters.

As used herein, the term "organic esters" refers to the esters formed between the compound of formula (I) or its 5' phosphate ester, and lower alkanoic acids and benzoic acid. The term "lower alkanoic acids" refers to alkanoic acids having from 1 to 4 carbon atoms.

As used herein, the term "esters" encompasses both organic esters and the 5' phosphate ester of the compound of formula (I) unless the context implies otherwise.

Pharmaceutically acceptable salts include salts of the 5'-phosphate ester of the compound of formula (I), e.g. the sodium, potassium, calcium and magnesium salts and acid addition salts of the compound of formula (I) and its organic esters such as the salts derived from hydrochloric, hydriodic, sulphuric, phosphoric, acetic, p-toluenesulphonic, methanesulphonic, maleic, lactic, citric, tartaric, succinic, oxalic, p-chlorobenzenesulphonic, isethionic, gluconic, pantothenic and lactobionic acids.

The mechanism of the anti-inflammatory action of 4-amino-1-(2-deoxy-δ-d-ribofuranosyl)-1H-imidazo-[4,5-c]-pyridine is at present unknown. It is not antipyretic and has no analgesic activity per se, and in this respect is like steroidal anti-inflammatory drugs such as prednisolone and hydrocortisone and like these known drugs will give relief from pain in many clinical syndromes by reducing inflammation. 4-Amino-1-(2-deoxy-β-D-ribofuranosyl)-1H-imidazo-[4,5-c]-pyridine does not inhibit prostaglandin metabolism in vitro through the lipoxygenase or cyclooxygenase pathway and is thus free of the side effects, particularly gastric damage and inhibition of platelet aggregation, associated with prostaglandin inhibitors such as aspirin. 4-Amino-1-(2-deoxy-β-D-ribofuranosyl)-1H-imidazo-[4,5-c]-pyridine is also free of the side effects of the anti-inflammatory steroids and unlike compounds such as acetaminophen (paracetamol) does not cause liver damage in the animal models used.

Although its mechanism of action is different to that of aspirin, 4-amino-1-(2-deoxy-β-D-ribofuranosyl)-1H-imidazo-[4,5-c]-pyridine is similar to aspirin in that it has a long duration of action (about 15 hours) associated with a short half life. Thus the compound of formula (I) will require relatively infrequent administration for example twice daily and the problem of morning stiffness and associated pain and crippling effects in patients with arthritic conditions may be alleviated, in contrast to the shorter acting non-steroidal and steroidal anti-inflammatory agents which do not possess this property. In addition 4-amino-1-(2-deoxy-β-D-ribofuranosyl)-1H-imidazo-[4,5-c]-pyridine by virtue of its different mode of action to aspirin, salicylates and steroids, may be combined with such drugs to provide a 'sparing effect' reducing the required dose of these drugs and hence the side effects associated therewith. The compound of formula (I) is also advantageous in possessing a high therapeutic index and thus is unlikely to present problems associated with accidental overdose.

4-Amino-1-(2-deoxy-β-D-ribofuranosyl)-1H-imidazo-[4,5-c-pyridine has the substantial advantage over known anti-inflammatory drugs that it is highly soluble in water unlike, for instance, aspirin and prednisolone.

The compound of formula (I), 4-amino-1-(2-deoxyβ-D-ribofuranosyl)-1H-imidazo-[4,5-c]-pyridine is the most preferred anti-inflammatory agent.

The compound of formula (I), its esters and pharmaceutically acceptable salts thereof are also useful as immunosuppressive agents.

The compound of formula (I), its esters, and pharmaceutically acceptable salts thereof, may be prepared by various chemical methods already known in the art of nucleoside chemistry. However these methods are generally not stereochemically specific thus yielding a mixture of isomers of the desired product. Furthermore, the yields are often poor and the processes are not usually suitable for use on large scale. With certain purine bases the problem of synthesis has been overcome by means of an enzymatic pentosylation (see for example European Patent Application No. 78 101 295.0) in which a purine nucleoside phosphorylase enzyme is used as the essential catalyst. Such a method has the advantages that it is stereochemically specific, gives improved yields of the nucleoside and is readily adaptable to use for large scale production.

It is well known that enzymes have a high degree of specificity and that small changes in the substrate(s) may markedly affect the enzyme's ability to catalyse a reaction.

However, it has been reported that modification of the purine base by removal of, or addition to the heterocyclic ring system of a nitrogen atom affects the ability of the base to act as a substrate for purine nucleoside phosphorylases. Thus a number of 1H-imidazo-[4,5-c]-pyridines have been shown not to be substrates for mammalian purine nucleoside phosphorylase [Townsend et al., Lectures in Heterocyclic Chemistry Vol. 4, supplement to *J. Hetero. Chem.* 15, S-19 to S-95, (1978)] and 7-deazaadenosine, 7-deazainosine and S-azaguanosine have been shown not to be substrates for microbial purine nucleoside phosphorylase [Doskocil and Holy, *Coll. Czeck. Chem. Commun.*, 42, 370, (1977)].

Further it has been shown that 1H-imidazo-[4,5-c]-pyridine nucleosides have conformations which differ from their purine counterparts, [Ludemann et al., *A. Naturforsch*, 33C, 305, (1978), May et al., *J. Amer. Chem. Soc.*, 98, 825 (1976)] suggesting that purines and 1H-imidazo-[4,5-c]-pyridines may be expected to behave differently in the relevant enzyme systems.

We have now surprisingly found that certain 4-substituted-1H-imidazo-[4,5-c]-pyridines are accepted as substrates by purine nucleoside phosphorylase and thus that 4-substituted-1-(2-deoxy-β-D-ribofuranosyl)-1H-imidazo-[4,5-c]-pyridines may be produced by an enzymatic method.

Accordingly, the present invention provides, in a second aspect, a process for producing compounds of formula (II)

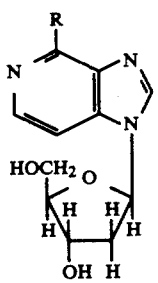

(II)

wherein R is halogen, amino or substituted amino, including protected amino, which process comprises reacting a 4-substituted-1H-imidazo-[4,5-c]-pyridine base of formula (III)

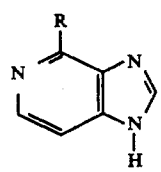

(III)

wherein R is as defined above, with a 2-deoxyribosyl donor system comprising 2-deoxyribose-1-phosphate and a purine nucleoside phosphorylase enzyme.

When R in a compound of formula (III) is amino, the product of the reaction is 4-amino-1-(2-deoxy-β-D-ribofuranosyl)-1H-imidazo-[4,5-c]-pyridine, the compound of formula (I). This particular reaction is not practicable by chemical means.

When R in a compound of formula (III) is halogen or substituted amino, including protected amino, the reaction produces novel compounds which are of biological interest in themselves. Furthermore, those compounds of formula (II) wherein R is halogen or protected amino are intermediates useful in the production of the compound of formula (I) as will become apparent below.

Compounds of formula (IIA)

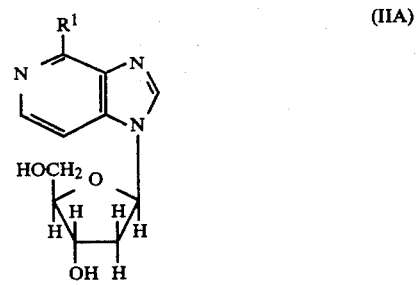

(IIA)

wherein $R^1$ is halogen or substituted amino, including protected amino are novel.

As used herein the term "substituted amino" encompasses groups such as mono- and di-loweralkyl amino and other conventionally substituted amino groups including protected amino groups. The term "protected amino" refers to substituted amino groups which may readily be converted to amino groups by processes known in the art of organic chemistry, thus, in particular it embraces aralkylamino groups such as benzylamino and benzyhydrylamino groups.

Compounds of formula (IIA) are of biological interest and those wherein $R^1$ is halogen or protected amino are also useful as intermediates in the synthesis of the compound of formula (I).

For use in the production of compounds of formula (II), 2-deoxyribose-1-phosphate may be provided by synthetic processes known in themselves in the literature [see, for instance, MacDonald, D. L., and Fletcher, H. G. Jr., *J. Amer. Chem. Soc.*, 82, 1832, (1960)]. However, it can be convenient or even advantageous if the 2-deoxyribose-1-phosphate is generated enzymatically from a 2-deoxyribosyl moiety donor and inorganic phosphate. Although this reaction may be carried out separately and the product added to the reaction mixture, it has been found advantageous to carry out the generation of 2-deoxyribose-1-phosphate and the production of the compound of formula (II) in a "one-pot" process by enzymatically forming the intermediate 2-deoxyribose-1-phosphate in situ.

The net effect of the coupled reactions therefore is the transfer of the 2-deoxyribosyl moiety of the donor 2'-deoxy-ribonucleoside to the free 4-substituted-1H-imidazo-[4,5-c]-pyridine base, of formula (III) thereby producing the desired 2'-deoxyribonucleoside.

The 2-deoxyribosyl moiety donor may be a purine 2'-deoxyribonucleoside for example, adenine 2'-deoxyribonucleoside, a pyrimidine 2'-deoxyribonucleoside for example, uracil 2'-deoxyribonucleoside, or a mixture of various 2'-deoxyribonucleosides and non-nucleosidic material. However, for the purposes of the present invention it is preferable that the 2'-deoxyribosyl moiety donor is substantially free from non-nucleosidic material and also that it is a pyrimidine 2'-deoxyribonucleoside.

The reasons for the preference for the use of a pyrimidine 2'-deoxyribonucleoside as the donor are two-fold. Firstly, the properties of the donor 2'-deoxyribonucleoside are sufficiently different from thos of the desired product to facilitate easy purification. Secondly, the donor base liberated during the course of the reaction is a pyrimidine rather than a purine which results in substantially less competition between the donor base and the acceptor base for the catalytic site on the enzyme directly involved in product synthesis (purine nucleoside phosphorylase).

The pyrimidine 2'-deoxyribonucleoside donors may be prepared by any of the methods known in the art, [see for instance, Drell, W., *J. Amer. Chem. Soc.*, 15, 2506, (1953)]. Purine 2'-deoxyribonucleoside donors may be prepared by any of the methods known in the art, [see for instance, Hotckiss, R. D., *J. Biol. Chem*, 175, 315, (1948)].

It has been found that both reactions described hereinabove are catalyzed by various enzymes which are present in microorganisms and mammalian tissues. The phosphorolysis of the donor 2'-deoxyribonucleoside is catalysed, for instance, by purine nucleoside phosphorylase if the donor is a purine 2'-deoxyribonucleoside, or by pyrimidine nucleoside phosphorylase, thymidine phosphorylase or uridine phosphorylase if the donor is a pyrimidine 2'-deoxyribonucleoside. The second reaction, by which the desired 4-substituted-1H-imidazo-[4,5-c]-pyridine 2'-deoxyribonucleoside is synthesised from the free base of formula (III) and 2-deoxyribose-1-phosphate, is catalysed by purine nucleoside phosphorylase.

The required 2'-deoxyribosyl transferring enzyme system therefore may consist of the latter phosphorylase alone, or in combination with any one of the former type, if the 2'-deoxyribosyl donor is a 2'-deoxyribonucleoside of a pyrimidine or pyrimidine analogue.

As previously stated, it has been found that the enzymes required for the catalysis of the reactions employed in the process of the present invention occur in microorganisms as well as mammalian tissues. For the purposes of the present invention, however, aerobic bacteria such as *B. stearothermophilus* and especially *E. coli B*, which is freely available from the American type culture collection under deposition No. ATCC 11303, were found to be excellent sources of such enzymes. The bacteria which provide the enzymes may be cultured under a variety of conditions. However, media which contained large quantities of glucose were found to be undesirable since the levels of the nucleoside phosphorylase enzymes in the bacterial cells were depressed in the presence of glucose.

It has been found that crude enzyme preparations are less suitable than purified preparations. This is due to the fact that crude preparations contain troublesome nucleic acids as well as enzymes other than those required for the process of the present invention. The extraneous enzymes in crude preparations catalyse undesirable alterations of substrates and products, and may even cause protcolysis of the required enzymes themselves. These factors decrease not only the yield of the desired products but also the ease with which they can be isolated from reaction mixtures.

In most cases therefore, it is desirable to purify the crude enzyme preparations before addition to the reaction mixture. This may be achieved in a number of ways known in themselves in the art. For instance, the desired enzymes may be separated or concentrated from extracts of the cells by a combination of treatment with calcium phosphate gel and ion exchange chromatography. Alternatively the cell extract may be treated with streptomycin or nuclease (DNA ase+RNA ase) prior to calcium phosphate gel treatment or by nuclease (DNA ase+RNA ase) treatment prior to ion exchange chromatography. Nuclease treatment is particularly advantageous if performed under dialyzing conditions at 4° to 40° C., preferably at 25° C. Gel filtration has been found to be especially useful as a late or final step in the purification when only relatively small volumes of liquid are involved.

The enzymes, provided in a sufficiently effective state and concentration, may then be used to catalyse the aforementioned reactions. A typical reaction mixture contains a 2'-deoxyribosyl moiety donor, a 4-substituted-1H-imidazo-[4,5-c]-pyridine base, inorganic phosphate, for example dipotassium hydrogen phosphate ($K_2HPO_4$), and the appropriate enzyme or enzymes in an aqueous medium or in a medium containing up to 50% of an organic solvent such as methanol, ethanol, propanol, butanol, acetone, methylethylketone, ethylacetate, toluene, tetrahydrofuran, dioxane, dimethyl sulfoxide, trichloromethane or cellosolve. The preferred concentration of organic solvent is 5% v/v. The inorganic phosphate concentration can be from 0.001 mM to 2,000 mM, preferably 1 to 200 mM. The reaction is performed at near neutral pH, that is, in the pH range of about 5 to 9, preferably 6.0 to 8.5 and at a temperature of 3° to 70° C., preferably 25° to 45° C. Mild conditions are preferable since the glycosidic bond of 4-substituted -1H-imidazo-[4,5-c]-pyridine-2'-deoxyribosides is labile under acid conditions, particularly at elevated temperatures, and the enzymes are unstable at extremes of temperature and pH. The preferable concentration of the enzyme is a function of the substrate efficiency of the particular 2'-deoxyribosyl moiety donors and acceptors used and the length of time that one wishes to allow the reaction to proceed. In some cases it is preferable to use larger amounts of the enzyme in order to reduce the reaction time because of the instability of certain of the products in aqueous solution. The purity of the enzymes used is a question of convenience. Crude extracts will catalyze the desired reactions but the yield of product is usually less and its isolation is more difficult than when purified enzymes are used for the reasons explained above. If the enzymes used are stored as ammonium sulphate suspensions, they are preferably added to the reactions as centrifuged pellets from the suspensions rather than as the whole suspensions.

Enzymes may be salvaged from reaction mixtures, for instance by batch adsorption onto DEAE-cellulose after the reaction has reached a satisfactory point and subsequent removal from the soluble components of the reaction mixture by centrifugation or by gel filtration of reaction mixtures. In some cases, enzymes may be recycled by virtue of the fact that the bulk of the product precipitates out from the reaction mixture and upon its removal, more starting material may be added to the reaction fluid in order that product formation may be resumed.

Usually it is preferable that all the components are contained in suspension or solution but when highly soluble substrates are used an alternative procedure wherein a solution of the reaction mixture components except enzymes is pumped slowly through a column containing a stationary phase to which the appropriate enzymes have been fixed, (for instance, when the enzymes are adsorbed to a DEAE-cellulose) may be preferable.

It has been found that, if it is so desired, enzymes may be conserved by allowing reactions to proceed for extended periods of time, for example, up to thirty days or longer. However, for reaction mixtures which are incubated for more than one day it is desirable to have an antimicrobial agent, for example sodium or potassium azide or toluene, in the reaction mixture, unless the reaction mixture is sterilised by filtration or some other technique known to the art.

The desired 4-substituted-1H-imidazo-[4,5-c]- pyridine-2'-deoxyribosides may be recovered or isolated by any of the known means for separating mixtures of chemical compounds into individual compounds. For example, the separation can be effected by utilizing differences in the solubilities in various solvents between the desired end product and impurities, the difference in their distribution coefficients between two solvent layers, the difference in their adsorbabilities to an adsorbent such as ion-exchange resins, the difference in their rates of passage through cross-linked resins such as polyacrylamide gels, or the difference in their crystallizabilities from a solvent. In cases where the product crystallizes out of the reaction mixture, it can be collected by centrifugation or by filtration with or without a filter aid. In practice, these means for separation or isolation are carried out in combination or repeatedly depending on the desired purity and state of the products.

As mentioned above the compound of formula (I) may be produced from compounds of formula (IIA) wherein $R^1$ is halogen or protected amino by conversion of the 4-substituent to an amino group.

According to the present invention in another aspect there is therefore provided a process for producing 4-amino-1-(2-deoxy-β-D-ribofuranosyl)-1H-imidazo-[4,5-c]-pyridine which comprises the conversion of the 4-substituent of a compound of formula (IV),

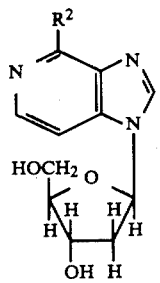

wherein $R^2$ is halogen or protected amino, into an amino group.

When $R^2$ is halogen this conversion may be effected by conventional means such as ammonolysis using ammonia at elevated temperatures and pressure or using hydrazine. In the latter case the 4-hydrazino derivative is formed and then reduced, advantageously using Raney nickel in a suitable solvent such as oxygen-free water.

It has been found particularly convenient to carry out this conversion by first introducing a protected amino group at the 4-position and reducing this to afford the compound of formula (I). Thus, for instance, the 4-halogeno compounds of formula (IV) may be treated with benzylamine or benzhydrylamine, i.e. (diphenylmethyl)amine. Reduction may be effected by conventional means including reduction using Raney nickel, metallic sodium in liquid ammonia, or hydrogen gas and an appropriate catalyst, such as palladium hydroxide, in a suitable solvent, such as an alcohol.

Compounds of formula (II) may also be produced by chemical methods of pentosylation known in the art of nucleoside synthesis.

Accordingly, the present invention, in a further aspect, provides a process for producing a compound of formula (II) as hereinbefore defined which process comprises reacting a compound of formula (V)

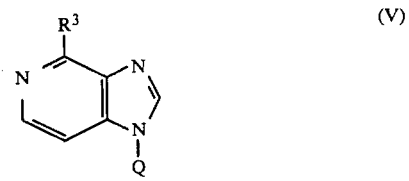

wherein R is halogen, amino or substituted amino, including protected amino and Q is a leaving atom or group capable of being replaced with a 2-deoxyribosyl moiety, with a compound of formula (VI)

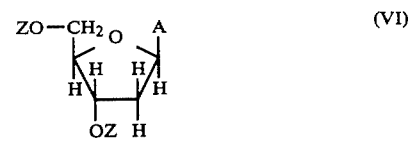

wherein A is an acyloxy group or a halogen atom and Z is a suitable protecting group.

Suitably, Q is a hydrogen or metal atom or a trialkylsilyl group and preferably is a trimethylsilyl group. If R is to be an amino or mono-substituted amino, i.e. if it will have a hydrogen atom bonded to the nitrogen atom, in the desired compound of formula (II) and Q is a trialkylsilyl group, then in the compound of formula (V) R will also bear a trialkylsilyl substituent which may be removed by a subsequent hydrolysis step as is known in the art.

When Q is hydrogen, A is suitably an acyloxy group, preferably the residue of a lower alkanoic acid and especially an acetoxy group.

When Q is a trialkylsilyl group, A is suitably a halogen atom and preferably a chlorine atom.

Z is suitably the residue of a carboxylic acid, preferably of an aromatic carboxylic acid such as para-toluoic acid (i.e. para-methyl benzoic acid).

It will be appreciated that compounds of formula (II) wherein R is a substituted amino group (including compounds of formula (IV) wherein $R^2$ is protected amine) may be produced by the enzymatic or chemical methods of pentosylation described above either directly from the appropriately substituted compound of formula (III) or (V), or by first producing a compound of formula (II) wherein R is a halogen atom and then converting the 4-halogeno substituent to the appropriate substituted amino group.

Esters of the compound of formula (1) and salts of the compound or its esters, may be produced by standard chemical methods.

Compounds of formula (III) wherein R is chlorine or amino, are known and may be prepared by methods known in the art, such as those described by Salemink and Van der Want, *Rec. Trav. Chim.*, 68, 1013, (1949); Mizuno et al., *Chem. Pharm. Bull.*, (Tokyo), 12, 866, (1964); Montgomery and Hewsen, *J. Med. Chem.*, 8, 708, (1965); and De Roos and Salemink, *Rec. Trav. Chim.*, 88, 1263, (1969). Further compounds of formula (III) may be produced by chemical means analogous to those used for converting compounds of formula (II) wherein R is halogen to those wherein R is amino or substituted amino as described above.

Compounds of formula (IV) are produced by direct pentosylation of appropriately substituted compounds of formula (III) or (V) or by conversion of a compound of formula (II) wherein R is halogen by methods described above.

Compounds of formula (V) wherein $R^3$ is chloro or amino are known in the art. Further compounds of formula (V) may be prepared by conversion of the 4-substituent as described above.

Compounds of formula (VI) are also known and may be prepared by known methods, [see for instance Hoffer, M., *Chem. Ber.*, 93, 2777, (1960), Ness, R. K. et al, *J. Org. Chem.*, 26, 2895, (1963), Robins M. G. and Robins R. K. in Synthetic Procedures in Nucleic Acid Chemistry, Vol. I, W. W. Zorback and R. S. Tipson Eds., Interscience Publishers, NY, NY, (1968) p. 519 and Robins, M. J. and Robins, R. K., *J. Amer. Chem. Soc.*, 87, 4934, (1965)].

The compounds of formula (I), its esters and pharmaceutically acceptable salts are useful in both short and long term treatment of inflammation.

The compound of formula (I) has also been demonstrated to be a potent inhibitor of mouse neutrophil chemotaxis, lymphocyte mediated cytolysis and of carrageenan-induced pleurisy and thus to have immunosuppressive activity.

While the compound of formula (I), its esters and pharmaceutically acceptable salts of the compound or its esters may be administered as the raw chemical, it is preferred that they be administered as pharmaceutical formulations.

Accordingly the present invention, in a further aspect, provides a pharmaceutical formulation comprising a compound of formula (I), an ester or a pharmaceutically acceptable salt of the compound or an ester thereof, hereinafter referred to as the "active compound", in association with a pharmaceutically acceptable carrier.

A carrier is a material useful for administering the active compound and must be "acceptable" in the sense of being compatible with the other ingredients of the formulation and not deleterious to the recipient thereof.

The pharmaceutical formulations are prepared by any of the methods well known in the art of pharmacy all of which involve bringing into association the active compound and the carrier therefor.

4-Amino-1-(2-deoxy-β-D-ribofuranosyl)-1H-imidazo-[4,5-c]-pyridine is effective as an anti-inflammatory agent not only orally and systemically but also locally and is thus particularly suitable for topical administration. The term "topical" as applied herein relates to the use of the active ingredient incorporated in a suitable pharmaceutical carrier, and applied at the site of the disease for the exertion of local action. Included within the scope of topical formulations are ophthalmic formulations.

Pharmaceutical formulations suitable for topical administration may be presented in anhydrous forms such as ointments, lotions, jellies, sprays, aerosols, and bath oils. The term ointment includes formulations (including creams) having oleaginous, absorption, water-soluble and emulsion type bases, for example petrolatum, lanolin, polyethylene glycols and mixtures thereof.

Ointments are semi-solid materials with the active compound dispersed therein. These and other topical formulations enable the active ingredient to be applied and retained locally at the site of the disease.

Topical formulations may contain a concentration of active compound of from 0.05 to 2% w/w preferably 0.1 to 1% w/w most preferably 0.2 to 0.5% w/w.

Other pharmaceutical formulations include those suitable for oral, rectal, and parenteral administration although of these oral is preferred. The formulations may, where appropriate, be conveniently presented in discrete dosage units and may be prepared by any of the methods well known in the art of pharmacy. A convenient unit dose formulation contains the active compound in an amount of from 5 mg to 250 mg, preferably 10 to 100 mg, most preferably about 50 mg to be taken once or several times daily.

Pharmaceutical formulations suitable for oral administration wherein the carrier is a solid are most preferably presented as unit dose formulations such as boluses, capsules, cachets or tablets each containing a predetermined amount of the active compound. A tablet may be made by compression or moulding optionally with one or more accessory ingredients. Compressed tablets may be prepared by compressing in a suitable machine the active compound in a free-flowing form such as powder or granules optionally mixed with a binder, lubricant, inert diluent, lubricating, surface active or dispersing agent. Tablets may be optionally coated and, if uncoated, may be optionally scored. Capsules may be prepared by filling the active compound either alone or in admixture with one or more accessory ingredients, into the capsule cases and then sealing them in the usual manner. Cachets are analogous to capsules wherein the active compound together with any accessory ingredient(s) are sealed in a rice paper envelope.

Pharmaceutical formulations suitable for oral administration wherein the carrier is a liquid may be presented as a solution or a suspension in an aqueous liquid, or as an oil-in-water or water-in-oil liquid emulsion.

Pharmaceutical formulations suitable for rectal administration wherein the carrier is a solid are most preferably presented as unit dose suppositories.

Suitable carriers include cocoa butter and other material commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

For the treatment of inflammatory conditions the active compound may be administered orally or parenterally to man at dosages in the range of 0.05 to 10 mg/kg body weight of recipient per day, particularly 0.2 to 5 mg/kg per day, most preferably 0.3 to 1 mg/kg per day, calculated as the free 2'-deoxyriboside. In contrast immuno-suppression requires more than 10 mg/kg body weight of recipient per day.

Accordingly there is provided as a further aspect of the present invention a method for the treatment of inflammation comprising the administration to a human or other mammal suffering from an inflammatory condition the compound of the formula (I), an ester or a pharmaceutically acceptable salt of the compound or an ester thereof.

By the term 'inflammation' is meant the reactive state of hyperaemia and exudation from its blood vessels, with consequent redness, heat, swelling and pain, which a tissue enters in response to physical or chemical injury or bacterial invasions.

Clinical conditions with which inflammation is associated, and hence for which an anti-inflammatory agent is indicated, include for example arthritis, including rheumatoid arthritis and osteoarthritis, post-operative inflammation, dental inflammation, acute and chronic ocular inflammatory diseases such as conjunctivitis.

Accordingly there is provided as a further aspect of the present invention a method for the suppression of the immune response in a human or other mammal comprising the administration of an immune response suppressing non-toxic amount of the compound of formula (I) or an ester thereof of a pharmaceutically acceptable salt of the compound or an ester thereof.

Conditions when the suppression of the immune response is desirable include autoimmune diseases such as Lupus erythematosis, Hemolytic anemia, Ulcerative colitis, Nephrosis and the prevention of rejection of foreign cells such as grafts including organ transplants.

The invention will now be illustrated with reference to the following examples which are not intended to limit the scope of the invention in any way.

EXAMPLE 1

4-Amino-1-(2-deoxy-β-D-ribofuranosyl)-1H-imidazo-[4,5-c]-pyridine

The reaction mixture consisted of an aqueous suspension (26.9 ml) of 4-amino-1H-imidazo[4,5-c]-pyridine dihydrochloride (2.4 mmoles), 2'-deoxythymidine (7.2 mmoles), dipotassium hydrogen phosphate (2.7 mmoles), potassium azide (0.13 mmoles), 1,120 International Units (I.U.) of $E.$ $coli.$ purine nucleoside phosphorylase (European Patent Application No. 78 101 295.0) and 3,750 I.U. of $E.$ $coli.$ thymidine phosphorylase (U.S. Pat. No. 4,097,337). The pH of the reaction mixture was adjusted to 6.70 before the addition of the enzymes. After 6 days at 37° C., the reaction mixture was filtered and then clarified by centrifugation at 48,000×g at 3° C. for 10 minutes. The supernatant was applied to a Sephadex G-10 column (5×90 cm). The column was eluted with water. Fractions containing product were combined and dried in vacuo. The residue was dissolved in water (5 ml) filtered through a Millipore millex filter (0.22 μm); dried in vacuo, redissolved in water (4 ml) and applied to a Dowex-1 hydroxide column (0.5×6 cm). The column was washed with water (10 ml) and then with 30% aqueous methanol. The fractions containing product were combined and dried in vacuo yielding 0.017 g of the one and one quarter hydrate of the product, 4-amino-1-(2-deoxy-β-D-ribofuranosyl)-1H-imidazo-[4,5-c]-pyridine.

Anal. Calcd for $C_{11}H_{13}N_4O_3 \cdot 1\frac{1}{4}H_2O$; Theory: C, 48.61; H, 5.75; N, 20.62% Found: C, 48.59; H, 5.77; N, 20.59.

| U.V. Spectra (nm): | Solvent | $\lambda_{max}$ | $\lambda_{min}$ | (Sh) |
|---|---|---|---|---|
| | 0.1 N HCl | 260 | 228 | 269 |
| | 0.1 N NaOH | 263 | 230 | |

| Thin Layer Chromatography: | Support | Solvent | $R_f$ |
|---|---|---|---|
| | Cellulose | $H_2O$ | 0.47 (one spot) |

EXAMPLE 2

4-Chloro-1-(2-deoxy-β-D-ribofuranosyl)-1H-imidazo-[4,5-c]pyridine

The reaction mixture consisted of an aqueous suspension (87 ml) of 4-chloro-1H-imidazo-[4,5-c]-pyridine (13 mmoles).

2'-deoxythymidine (23.5 moles), potassium phosphate (8 mmoles), potassium azide (0.13 mmoles), 2,120 I.U. of $E.$ $coli$ purine nucleoside phosphorylase (European patent application No. 78 102 295.0) and 26,000 I.U. of $E.$ $coli$ thymidine phosphorylase (U.S. Pat. No. 4,097,337). Before the addition of the enzymes, the pH was adjusted to 6.4. The suspension was incubated at 37° C. for 24 hours and then n-propanol (6 ml) was added. After 6 more days at 37° C., the reaction mixture was filtered and the filtrate set at 3° C. for 18 hours. After a second filtration, the filtrate was applied to a Sephadex column (G-10) (5×90 cm) and eluted with water. Fractions containing the product were combined and evaporated to dryness in vacuo. The residue was dissolved in 30% aqueous n-propanol (12 ml) and applied to a column packed with polyacrylamide (P-2 BioRad Laboratories) (2.5×90 cm) and eluted with 30% aqueous n-propanol. Fractions containing the product without yellow colour were combined and evaporated in vacuo until the bulk of the propanol was removed. The remaining water was removed by lyophilization. 1.59 g of product, 4-chloro-1-(2-deoxy-β-D-ribofuranosyl)-1H-imidazo-[4,5-c]-pyridine, were obtained.

Anal. Calcd. for $C_{11}H_{12}N_3O_3Cl$; Theory: C, 48.99; H, 4.49; N, 15.58; Cl, 13.15%; Found: C, 48.85; H, 4.52; N, 15.54; Cl, 13.19%.

| U.V. Spectra (nm): | Solvent | $\lambda_{max}$ | $\lambda_{min}$ | (Sh) |
|---|---|---|---|---|
| | 0.1 N HCl | 273.5 | 231.5 | |
| | 0.1 N NaOH | 255 | 226.5 | |
| | | 265.5 | 262.5 | 273 |

EXAMPLE 3

4-amino-1-(2-deoxy-β-D-ribofuranosyl)-1H-imidazo-[4,5-c]-pyridine

A solution of 4-chloro-1-(2-deoxy-β-D-ribofuranosyl)-1H-imidazo-[4,5-c]-pyridine (1.6 g) in 85% v/v aqueous hydrazine hydrate (60 ml) was heated at reflux in a nitrogen atmosphere for 1 hour. The solution was taken to dryness in vacuo and the residue was dissolved in oxygen free water (120 ml). Raney Nickel (6 g, wet) was added and the reaction mixture was refluxed for 1 hour. The hot mixture was filtered through a bed of Celite and the catalyst was washed well with hot water. The cooled filtrate was saturated with hydrogen sulfide gas and allowed to stand for 20 hours.

The black precipitate was removed and the solution was taken to dryness in vacuo. Water was added and a coloured insoluble material was removed by filtration. The filtrate was evaporated in vacuo to give 1.2 g of solid This was dissolved in water (8 ml), filtered and purified by reversed phase chromatography using water and aqueous methanol as the eluent. The appropriate fractions were lyophilized to give the product, 4-amino-1-(2-deoxy-β-D-ribofuranosyl)-1H-imidazo-[4,5-c]-pyridine.

| U.V. Spectra (nm): Solvent | $\lambda_{max}$ | $\lambda_{min}$ | (Sh) |
|---|---|---|---|
| 0.1 N HCl | 261 nm | 227 nm | 270 nm |
| 0.1 N NaOH | 262.5 nm | 230 nm | |

EXAMPLE 4

Preparation of 4-benzylamino-1H-imidazo[4,5-c]-pyridine

A mixture of 4-chloro-1H-imidazo-[4,5-c]-pyridine (2.0 g, 13 mmole), benzylamine (5 ml) and a few drops of water was heated at reflux for 4 days. The reaction mixture was poured onto ice and water and the cold mixture was extracted twice with diethylether. The ether was removed in vacuo and the residual oil was triturated twice with hexane. The oil was suspended in water and the aqueous phase was neutralised with glacial acetic acid. The aqueous phase was taken to dryness in vacuo and resuspended in water (15 ml). It was applied to a column of Dowex 50 (H+) (10 g). The column was washed with water until the ultra violet absorbance of the eluant had fallen to zero. The column packing was removed from the column and heated with several portions of concentrated ammonium hydroxide solution (400 ml). The basic solution was filtered in vacuo, cooled and neutralized with glacial acetic acid. The yellow solid was collected and dried in vacuo at 40° C. Yield of 4-benzylamino-1H-imidazo-[4,5-c]-pyridine 0.94 g, m.p. 60°-64° C., 31.5%.

Analysis calculated for $C_{13}H_{12}N_4.0.3H_2O$: Theory: C, 67.98; H, 5.53; N, 24.40%; Found: C, 68.05; H, 5.26; N, 24.23%.

| U.V. Data: Solvent | $\lambda_{max}$ | E | Shoulder | E |
|---|---|---|---|---|
| 0.1 N HCl | 277 | 13000 | 263 | 12100 |
| 0.1 N NaOH | 278 | 11900 | | |

EXAMPLE 5

4-Benzylamino-1-(2-deoxy-β-D-ribofuranosyl)-1H-imidazo-[4,5-c]-pyridine

A reaction mixture was prepared comprising thymidine (5.13 g), 4-benzylamino-1H-imidazo-[4,5-c]-pyridine (0.7 g), potassium hydrogen phosphate ($K_xH_yPO_4$, 0.2M, 6 ml), (pH 7.4)-disodiumethylenediaminetetraacetic acid ($Na_2EDTA$, 0.13 mM), water (200 ml) n-propanol (10 ml), purine nucleoside phosphoryase (as described in Example 1, 2,800 I.U.) and thymidine phosphorylase (as described in Example I, 12,550 I.U.).

This suspension was incubated at 37° and after 5 days was filtered.

n-Propanol and about half the water was removed from the filtrate in vacuo. The remaining solution formed some precipitate after standing at 25° C. for 20 hours. This material was removed by filtration and was found to be mostly thymine. The filtrate was stored at 3° for 20 hours. The crystals that formed were collected by filtration, washed with water, and dried in vacuo affording 0.37 g of 4-benzylamino-1-(2-deoxy-β-D-ribofuranosyl)-1H-imidazo-[4,5-c]-pyridine.

Anal. Calcd. for $C_{18}H_{20}N_4O_3 3/2H_2O$: Theory: C, 58.81; H, 6.31; N, 15.24%; Found: C, 59.01; H, 6.31; N, 15.23%.

| U.V. Spectra (nm) Solvent | $\lambda_{max}$ | $\lambda_{min}$ | (Sh) |
|---|---|---|---|
| 0.1 N HCl | 269 | 236 | 260; 291 |
| 0.1 N NaOH | 274 | 237 | |

EXAMPLE 6

Immunosuppressive activity of 4-amino-1-(2-deoxy-β-D-ribofuranosyl)-1H-imidazo[4,5-c]-pyridine Assay of lymphocyte mediated cytolysis (LMC) in vitro The test compounds were assayed in vitro by the method described in Science,(N.Y.) 187, 957 (1975). The order of addition of reagents was (1) cytotoxic lymphocytes; (2) test compound dissolved in pyrogen-free saline; (3) $^{51}$Cr-labelled EL4 cells. In those experiments where an adenosine deaminase (ADA) inhibitor was required erythro-9-(2-hydroxy-3-nonyl)adenine (EHNA) was added before step (2) to give a final concentration of 7.9 μM.

The results are shown in Table 1 below.

TABLE I

| Test Compound | Conc. (μM) | % lysis Reduction |
|---|---|---|
| Adenosine* | 18.8 | 59 |
| | 9.4 | 59 |
| 2-Fluoro-adenosine | 2 | 60 |
| | 1 | 48.9 |
| 2-Chloro-adenosine | 9.4 | 64.4 |
| | 4.7 | 62.2 |
| 4-Amino-1-(2-deoxy-β-D-ribofuranosyl)-1H—imidazo-[4,5-c]-pyridine. | 37.5 | 73 |
| | 18.8 | 53 |

*tested in presence of ADA Inhibitor.

EXAMPLE 7

The Effect of 4-Amino-1-(2-deoxy-β-D-ribofuranosyl)-1H-imidazo-[4,5-c]-pyridine on Antibody-Dependent Cellular Cytotoxicity The title compound was tested in vitro in Antibody-Dependent Cellular Cytotoxicity assay [Perlmann, P. and Holm, G., Adv. Immunol., 11, 117, (1969)]. Mouse spleen cells from non-immunized animals served as the source of effector cells, assayed with chromium-labelled heterologous (sheep) erythrocytes target cells coated with mouse anti-sheep erythrocyte serum. The final concentration of the anti-serum in the incubation mixture was 1:66, the ratio of effector to target cells 25:1. After 4 hours of incubation at 37° C. in humidified atmosphere with 5% $CO_2$ with 100 μM concentration of 4-amino-1-(2-deoxy-β-D-ribofuranosyl)-1H-imidazo-[4,5-c]-pyridine present in the tissue culture medium, an inhibition of 83.2% of target cell-specific chromium release was found.

In a dose-response study, the IC$_{50}$ of 4-amino-1-(2-deoxy-$\beta$-D-ribofuranosyl)-1H-imidazo-[4,5-c]-pyridine was established to be in the range of 6.2 to 12.5 $\mu$M.

| Dose ($\mu$M) | 4-amino-1-(2-deoxy-$\beta$-D-ribofuranosyl)-1H—imidazo-[4,5-c]-pyridine | (4-amino-1-$\beta$-D-ribofuranosyl-1H—imidazo-[4,5-c]-pyridine |
|---|---|---|
| | (% inhibition of cellular cytotoxicity) | |
| 3.1 | 31.2 | 52.3 |
| 6.2 | 42.1 | 64.8 |
| 12.5 | 55.9 | 66.4 |
| 25.0 | 60.2 | not tested |

EXAMPLE 8

Acute Anti-inflammatory Activity of 4-amino-1-(2-deoxy-$\beta$-D-ribofuranosyl)-1H-imidazo-[4,5-c]-pyridine-Carrageenan Pleurisy Assay (CPA)

Following the procedure described by Vinegar et al in Proc. Soc. Exp. Biol. Med., 143, 711, (1973), and recently modified (Vinegar et al., Eur. J. Rheum. Inflam. 1, 204 (1978)) the acute anti-inflammatory activity of 4-amino-1-(2-deoxy-$\beta$-D-ribofuranosyl)-1H-imidazo-[4,5-c]-pyridine was compared with that of known anti-inflammatory drugs. The average 3 hour exudate volume for each drug-treated group was determined and the % inhibition relative to solvent-fed control animals calculated, the ED$_{50}$ (mg/kg of body weight) being the dose required to reduce the 3 hour exudate volume by 50%. There were 5 animals in each drug-treated group and the control group. The results are shown in Table II:

TABLE II

| | 4-amino-1-(2-deoxy-$\beta$-D-ribofuranosyl)-1H—imidazo-[4,5-c]-pyridine (mg/kg) | Aspirin (mg/kg) | Prednisolone (mg/kg) | Hydrocortisone (mg/kg) |
|---|---|---|---|---|
| 3 hr. Vol. p.o. | ~12 | 28 ± 3.2 | 3 ± 0.5 | 14 ± 10.2 |

EXAMPLE 9

| Tablet formulation | Amount per tablet |
|---|---|
| 4-amino-1-(2-deoxy-$\beta$-D-ribofuranosyl)-1H—imidazo-[4,5,-c]-pyridine | 100 mg |
| Lactose | 85 mg |
| Potato Starch, dried | 14.3 mg |
| Magnesium Stearate | 0.7 mg |
| Total | 200 mg |

EXAMPLE 10

| Syrup | Amount per tablet |
|---|---|
| 4-amino-1-(2-deoxy-$\beta$-D-ribofuranosyl)-1H—imidazo-[4,5-c]-pyridine | 10 mg |
| Glycerine | 1 g |
| Sucrose | 7 g |
| Methyl paraben | 10 mg |
| Sodium Benzoate | 10 mg |
| Flavour, Cherry, | 0.01 ml |
| Colouring | q.s. |

-continued

| Syrup | Amount per tablet |
|---|---|
| Water, purified. | q.s. to 10 ml |

EXAMPLE 11

| Injection | Amount per ampoule |
|---|---|
| 4-amino-1-(2-deoxy-$\beta$-D-ribofuranosyl)-1H—imidazo-[4,5-c]-pyridine | 10 mg |
| Sodium Chloride | 8.5 mg |
| Water for injection | q.s. to 10 ml |

EXAMPLE 12

| Water Soluble Ointment | Amount - (g) |
|---|---|
| 4-amino-1-(2-deoxy-$\beta$-D-ribofuranosyl)-1H—imidazo-[4,5-c]-pyridine | 0.5 |
| Polyethylene glycol 300 | 20.0 |
| Polyethylene glycol 1500 | 79.5 |
| Total | 100.0 |

EXAMPLE 13

| Skin Cream | amount (g) |
|---|---|
| 4-amino-1-(2-deoxy-$\beta$-D-ribofuranosyl)-1H—imidazo-[4,5-c]-pyridine | 0.5 |
| Glyceryl monostearate | 20.0 |
| Methylparaben | 0.3 |
| Petrolatum light liquid | 4.0 |
| Propylene glycol | 5.0 |
| Span 60 | 2.0 |
| Tween 61 | 4.0 |
| Water | 64.6 |
| Total | 100.0 |

What we may claim may comprise any novel feature disclosed herein, principally but not exclusively for example:

(i) The compound of formula (I) as hereinbefore defined, its esters and pharmaceutically acceptable salts of the compound or its esters.

(ii) The process for producing compounds of formula (II) as hereinbefore defined comprising the reaction of a compound of formula (III) as hereinbefore defined with a 2-deoxyribosyl donor system as hereinbefore defined.

(iii) Compounds of formula (IIA) as hereinbefore defined.

(iv) The process for producing 4-amino-1-(2-deoxy-$\beta$-D-ribofuranosyl)-1H-imidazo-[4,5-c]-pyridine comprising the conversion of the 4-substituent of a compound of formula (IV) as hereinbefore defined into an amino group.

(v) The process for producing a compound of formula (IV) as hereinbefore defined comprising the reaction of a compound of formula (V) as hereinbefore defined with a compound of formula (VI) as hereinbefore defined.

(vi) The compound of formula (V), its esters and pharmaceutically acceptable salts of the compound or its esters for use in medicine.

(vii) A pharmaceutical formulation comprising the compound of formula (I) or an ester thereof or a pharmaceutically acceptable salt of the compound or an ester thereof in association with a pharmaceutically acceptable carrier.

(viii) A method for the treatment of inflammation comprising the administration to a human or other mammal suffering from an inflammatory condition the compound of formula (I) an ester thereof or a pharmaceutically acceptable salt of the compound or an ester thereof.

We claim:

1. The compound of formula (I)

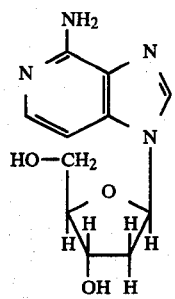

(I)

the 5'-phosphate ester thereof, organic esters of the compound or its 5'-phosphate ester with lower alkanoic or benzoic acid and pharmaceutically acceptable salts of the compound or its esters.

2. A compound of formula (IIA)

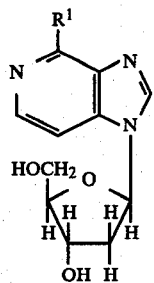

(IIA)

wherein $R^1$ is halogen.

3. A method for the treatment of inflammation comprising the administration to a human or other mammal suffering from an inflammatory condition an effective anti-inflammatory, non-toxic amount of an active ingredient selected from the compound of formula (I)

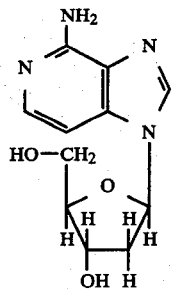

(I)

the 5'-phosphate ester of said compound, organic esters of said compound or its 5'-phosphate ester with lower alkanoic or benzoic acid and pharmaceutically acceptable salts of said compound or its esters.

4. A method according to claim 3 wherein said active ingredient is administered orally or parenterally in a dosage of from about 0.05 mg/kg to about 10 mg/kg body weight of recipient per day.

5. A method according to claim 3 wherein said active ingredient is administered topically for the exertion of local action.

6. A method according to claim 3 wherein said inflammatory condition is arthritis.

7. A method according to claim 3 comprising the administration of a pharmaceutical formulation comprising the active ingredient in association with a pharmaceutically acceptable carrier therefor.

8. A method for the suppression of the immune response in a human or other mammal comprising the administration of an immune response suppressing nontoxic amount of an active ingredient selected from the compound of formula (I),

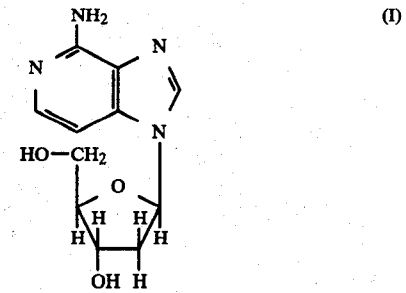

(I)

the 5'-phosphate ester of said compound, organic esters of said compound or its 5'-phosphate ester with lower alkanoic or benzoic acid and pharmaceutically acceptable salts of said compound or its esters.

9. A method according to claim 8 wherein said active ingredient is administered orally or parenterally in a dosage of at least 10 mg/kg body weight of recipient per day.

10. A method according to claim 8 for treating autoimmune disease or preventing rejection of foreign cells.

11. A pharmaceutical formulation for use in treatment of inflammation or suppression of the immune response or both comprising an effective inflammation or immune response nontoxic treatment amount of an ingredient selected from the compound of formula (I)

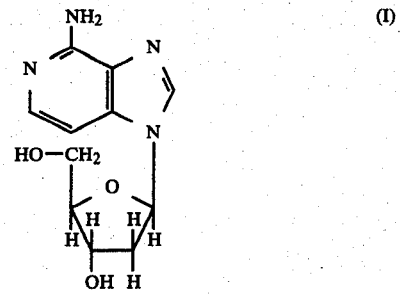

(I)

the 5'-phosphate ester thereof, organic esters of the compound or its 5'-phosphate ester with lower alkanoic or benzoic acid and pharmaceutically acceptable salts of the compound or its esters and a pharmaceutically acceptable carrier therefore.

* * * * *